United States Patent
Haran

(10) Patent No.: US 7,494,567 B2
(45) Date of Patent: Feb. 24, 2009

(54) COMBINED PAPER SHEET TEMPERATURE AND MOISTURE SENSOR

(75) Inventor: Frank M. Haran, North Vancouver (CA)

(73) Assignee: Honeywell ASCA Inc., Ontario (CA)

( * ) Notice: Subject to any disclaimer, the term of this patent is extended or adjusted under 35 U.S.C. 154(b) by 431 days.

(21) Appl. No.: 11/364,930

(22) Filed: Feb. 28, 2006

(65) Prior Publication Data

US 2007/0137823 A1 Jun. 21, 2007

Related U.S. Application Data

(60) Provisional application No. 60/750,843, filed on Dec. 15, 2005.

(51) Int. Cl.
*D21F 7/06* (2006.01)
(52) U.S. Cl. .............. 162/263; 162/198; 250/339.1; 324/694; 700/128; 700/129
(58) Field of Classification Search ............. 162/198, 162/263; 250/339.04, 339.1; 324/694
See application file for complete search history.

(56) References Cited

U.S. PATENT DOCUMENTS

| | | | | |
|---|---|---|---|---|
| 4,879,471 A * | 11/1989 | Dahlquist | ............. | 250/359.1 |
| 4,928,013 A | 5/1990 | Howarth et al. | | |
| 5,013,403 A * | 5/1991 | Chase | ............. | 162/49 |
| 5,094,535 A * | 3/1992 | Dahlquist et al. | ............. | 356/451 |
| 5,118,200 A | 6/1992 | Kirillov et al. | | |
| 5,124,552 A | 6/1992 | Anderson | | |
| 5,166,748 A * | 11/1992 | Dahlquist | ............. | 356/451 |
| 5,235,192 A | 8/1993 | Chase et al. | | |
| 5,568,978 A | 10/1996 | Johnson et al. | | |
| 5,795,394 A | 8/1998 | Belotserkovsky et al. | | |
| 5,892,679 A * | 4/1999 | He | ............. | 700/29 |
| 6,059,931 A * | 5/2000 | Hu et al. | ............. | 162/198 |
| 6,080,278 A * | 6/2000 | Heaven et al. | ............. | 162/198 |
| 6,092,003 A * | 7/2000 | Hagart-Alexander et al. | ............. | 700/129 |
| 6,149,770 A * | 11/2000 | Hu et al. | ............. | 162/199 |
| 6,204,672 B1 | 3/2001 | Chase | | |
| 6,466,839 B1 * | 10/2002 | Heaven et al. | ............. | 700/128 |
| 6,805,899 B2 * | 10/2004 | MacHattie et al. | ............. | 427/8 |
| 6,853,543 B1 * | 2/2005 | Moore et al. | ............. | 361/680 |
| 2004/0089806 A1 | 5/2004 | Murakami et al. | | |

FOREIGN PATENT DOCUMENTS

| | | |
|---|---|---|
| EP | 0518393 A1 | 12/1992 |
| WO | WO 03/064738 A2 | 8/2003 |
| WO | WO 2006/118619 A1 | 11/2006 |

* cited by examiner

*Primary Examiner*—Mark Halpern
(74) *Attorney, Agent, or Firm*—Cascio, Schmoyer & Zervas

(57) ABSTRACT

Temperature measurements of sheet material such as paper can be obtained directly from an analysis of the absorption spectrum of water in the infrared region. The technique is based in part on the recognition that the central wavelength position of a selected moisture peak is dependent upon the sheet temperature; the wavelength position also has a known temperature sensitivity. Thus, once the wavelength position of this moisture peak is ascertained, the moisture temperature of the product being monitored can be calculated. The position of the moisture peak is preferably obtained from the derivative of the peak. By measuring the size of the infrared absorption and the wavelength position of the absorption peak, both the moisture content and the moisture temperature of the sheet material can be determined. The data is used for process control. Tunable laser diodes are particularly suited as the source of infrared radiation for the temperature sensors.

17 Claims, 3 Drawing Sheets

COMBINED PAPER SHEET TEMPERATURE AND MOISTURE SENSOR

REFERENCE TO RELATED APPLICATION

This application claims priority to U.S. Provisional application Ser. No. 60/750,843 filed on Dec. 15, 2005.

FIELD OF THE INVENTION

The present invention generally relates to sensors and methods for measuring the moisture temperature of compositions and for measuring the presence and concentrations of specific components such as moisture or other spectroscopic measurable characteristic in the composition. The technique employs a device that directs infrared radiation from a tunable laser diode within specific wavelength bands onto a moving sheet of material such as paper and detects the radiation which emerges from the material. Analysis of the radiation spectrum yields the moisture temperature and moisture content.

BACKGROUND OF THE INVENTION

In the manufacture of paper on continuous papermaking machines, a web of paper is formed from an aqueous suspension of fibers (stock) on a traveling mesh papermaking fabric and water drains by gravity and suction through the fabric. The web is then transferred to the pressing section where more water is removed by pressure and vacuum. The web next enters the dryer section where steam heated dryers and hot air completes the drying process. The paper machine is, in essence, a water removal, system. A typical forming section of a papermaking machine includes an endless traveling papermaking fabric or wire, which travels over a series of water removal elements such as table rolls, foils, vacuum foils, and suction boxes. The stock is carried on the top surface of the papermaking fabric and is de-watered as the stock travels over the successive de-watering elements to form a sheet of paper. Finally, the wet sheet is transferred to the press section of the papermaking machine where enough water is removed to form a sheet of paper. Many factors influence the rate at which water is removed which ultimately affects the quality of the paper produced.

It is well known to continuously measure certain properties of the paper material in order to monitor the quality of the finished product. These on-line measurements often include basis weight, moisture content, and sheet caliper, i.e., thickness. The measurements can be used for controlling process variables with the goal of maintaining output quality and minimizing the quantity of product that must be rejected due to disturbances in the manufacturing process. The on-line sheet property measurements are often accomplished by scanning sensors that periodically traverse the sheet material from edge to edge.

It is conventional to measure the moisture content of sheet material upon its leaving the main dryer section or at the take up reel employing scanning sensors. Such measurement may be used to adjust the machine operation toward achieving desired parameters. One technique for measuring moisture content is to utilize the absorption spectrum of water in the infrared (IR) region. A monitoring or gauge apparatus for this purpose is commonly employed. Such an apparatus conventionally uses either a fixed gauge or a gauge mounted on a scanning head which is repetitively scanned transversely across the web at the exit from the dryer section and/or upon entry to the take up reel, as required by the individual machines. The gauges typically use a broadband infrared source such as a quartz tungsten halogen lamp and one or more detectors with the wavelength of interest being selected by a narrow-band filter, for example, an interference type filter. The gauges used fall into two main types: the transmissive type in which the source and detector are on opposite sides of the web and, in a scanning gauge, are scanned in synchronism across it, and the scatter type (typically called "reflective" type) in which the source and detector are in a single head on one side of the web, the detector responding to the amount of source radiation scattered from the web. While it is most common to position IR moisture gauges in the more benign dry-end environment, similar gauges are also employed in the wet-end of the papermaking machine. The wet-end moisture gauges are typically located at the end of the press section or the beginning of the dryer section. Gauges in these locations are useful for diagnosis of press and forming sections of the paper machine, or for "setting up" the web for entry into the dryer section.

In operation, the intensity of the infrared beam is not only dependent upon the moisture content and basis weight of the web, the absorption of infrared radiation by the moist web also varies with wavelength. The water and web fibers absorb certain wavelengths of the infrared spectrum more effectively than other wavelengths so that there are absorption peaks and valleys at various wavelengths along the spectrum. Moreover, these peaks and valleys shift to shorter wavelengths with increases in web temperature and to longer wavelengths with decreases in web temperature. It is important for infrared moisture measuring devices to compensate for shifts in the infrared absorption spectrum resulting from changes in web temperature. Because on-line paper web temperatures may range from 10° C. to as high as 100° C., the moisture measurements of these devices are subject to significant error otherwise.

U.S. Pat. No. 4,928,013 to Howarth et al. describes an infrared moisture sensor with two band pass filters which are selected to compensate for web temperature changes. In this sensor, a first band pass filter, associated with a measure detector, is selected so that it is approximately centered about the infrared absorption peak for water, at about 1.93 microns. As the web temperature increases, the intensity of detected infrared radiation increases at the long wavelength side of the pass band filter, while an approximately equal decrease in the detected infrared occurs at the opposite short wavelength side of the pass band. With this technique, the total amount of infrared radiation reaching the measure detector is said to be substantially insensitive to web temperature. A second band pass filter, associated with a reference detector, is selected so that it is in a region of the infrared spectrum close to the measure filter but far enough away from the measure filter that it is not effected by water absorption. Signal variations on this reference channel will be dominated by web variation other than those associated with water, these same losses are also present in the measure channel. These non-water dependent signal losses are likely dominated by scattering which will be dependent upon the basis weight of the sheet.

U.S. Pat. No. 5,124,552 to Anderson describes a technique for determining the moisture content of a web by detecting the amount of infrared radiation transmitted through the web, or reflected from the web, in three separate wavelength regions of the infrared spectrum. Temperature insensitivity is said to be achieved by carefully selecting the temperature response of a first band pass filter, the measurement filter, and a second band pass filter, the reference filter, based on the maximum basis weight and maximum moisture content of the web and further compensating for any remaining temperature sensitivity with a third band pass filter, the temperature correction filter.

In a papermaking, the moisture sensor output is typically used to control the moisture level via an actuation mechanism, e.g., injection of steam into the paper, which in turn influences the sheet temperature. Moreover, with prior art techniques of measuring moisture, minimizing temperature sensitivity comes at the expense of moisture sensitivity. The art is in search of an improved moisture temperature sensor. It is desirable to eliminate this moisture/temperature cross sensitivity.

SUMMARY OF THE INVENTION

The present invention is directed to techniques for temperature measurements that can be obtained directly from an analysis of the absorption spectrum of water in the infrared (IR) region. The invention is based in part on the recognition that the central wavelength position of a selected moisture peak is dependent upon the paper or sheet temperature; the wavelength position also has a known temperature sensitivity. Thus, once the wavelength position of this moisture peak is ascertained, the moisture temperature of the product being monitored can be calculated. The position of the moisture peak is preferably obtained by evaluating where the derivative of the peak equals zero. With the present invention, by measuring the size of the IR absorption and the wavelength position of the absorption peak, both the moisture content and the moisture temperature of the product can be determined.

In one aspect, the invention is directed to a high speed, real time method of determining the moisture temperature of a composition that includes the steps of:

(a) directing radiation from an external light source having a desired wavelength region that surrounds an absorption peak for water to be incident upon the composition;

(b) analyzing the radiation that emerges from the composition to determine a central wavelength position of the radiation of the absorption peak; and (c) computing the moisture temperature from the central wavelength position.

In another aspect, the invention is directed to a high speed, real time method for adjusting at least one of the moisture content and temperature of a web that includes the steps of:

(a) directing radiation from an external light source having a desired wavelength region that surrounds an absorption peak for water to be incident upon the web;

(b) analyzing the radiation that emerges from the web to determine a central wavelength position of the radiation of the absorption peak;

(c) computing the moisture temperature from the central wavelength position;

(d) determining the moisture content of the web; and (e) altering at least one of moisture content and temperature of at least a portion of the web based upon the computed moisture temperature and determined moisture content.

In a further aspect, the invention is directed to a high speed sensor that measures the temperature of a moisture containing composition that includes:

(a) an external light source for directing radiation having a desired wavelength region that surrounds an absorption peak for water to be incident upon the composition;

(b) means for analyzing the radiation that emerges from the composition to determine a central wavelength position of the radiation of the absorption peak; and (c) means for computing the moisture temperature from the central wavelength position.

In a yet another aspect, the invention is directed to a high speed sensor that measures the temperature and moisture content of a moisture containing composition that includes:

(a) an external light source for directing radiation having a desired wavelength region that surrounds an absorption peak for water to be incident upon the composition;

(b) means for analyzing the radiation that emerges from the composition to determine a central wavelength position of the radiation of the absorption peak;

(c) means for computing the moisture temperature from the central wavelength position; and (d) means for measuring the moisture content.

DETAILED DESCRIPTION OF PREFERRED EMBODIMENTS

The present invention is directed to a sensor system for detecting properties of a composition, especially material that is in the form of a film, web or sheet. While the sensor will be illustrated in measuring the moisture temperature and moisture content in paper, it is understood that the sensor can be employed to measure the presence and content of a variety of spectroscopic measurable components in a number of different materials including, for example, coated materials, plastics, fabrics, and the like.

Figure 1:
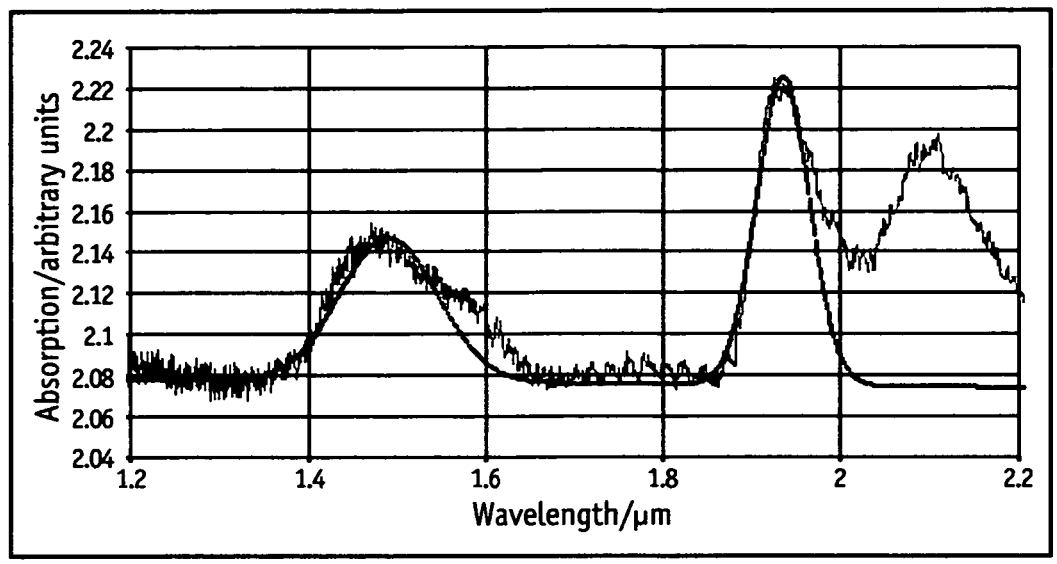
FIG. 1 is the absorption spectrum of a moisturized paper sample wherein the y-axis is not calibrated.

FIG. 1 shows the transmission Fourier-transform infrared spectroscopy (FTIR) spectrum for a moisturized paper sample. As is evident, there are two moisture dependent peaks, the first one being in the 1.4 to 1.5 μm wavelength region that has a full-width-half-maximum (FWHM) peak width of approximately 55 nm, and the second one being at approximately 1.94 μm that has a FWHM of approximately 30 nm. The amplitude of each moisture peak is proportional to the moisture content of the paper. The central wavelength position of the moisture peak is influenced by the paper temperature and has a temperature sensitivity of approximately −0.3 nm/° C. The 1.4 μm absorption peak has been measured to have a greater temperature sensitivity of −0.47 nm/° C. but this may be attributed to the fact that this peak has both cellulose and water dependence.

The experimental spectral data in FIG. 1 was fitted using a superposition of Gaussian line-shapes with a DC offset. The equation used to fit the peak was:

$$I = I_p \exp\left(\frac{-(\lambda - \lambda_0)^2}{2 \cdot \Delta\lambda^2}\right),$$

where $I_p$ is the intensity at the central wavelength, $\lambda_0$, $\lambda$ is the wavelength and $\Delta\lambda$ is the FWHM of the absorption line.

Figure 2:
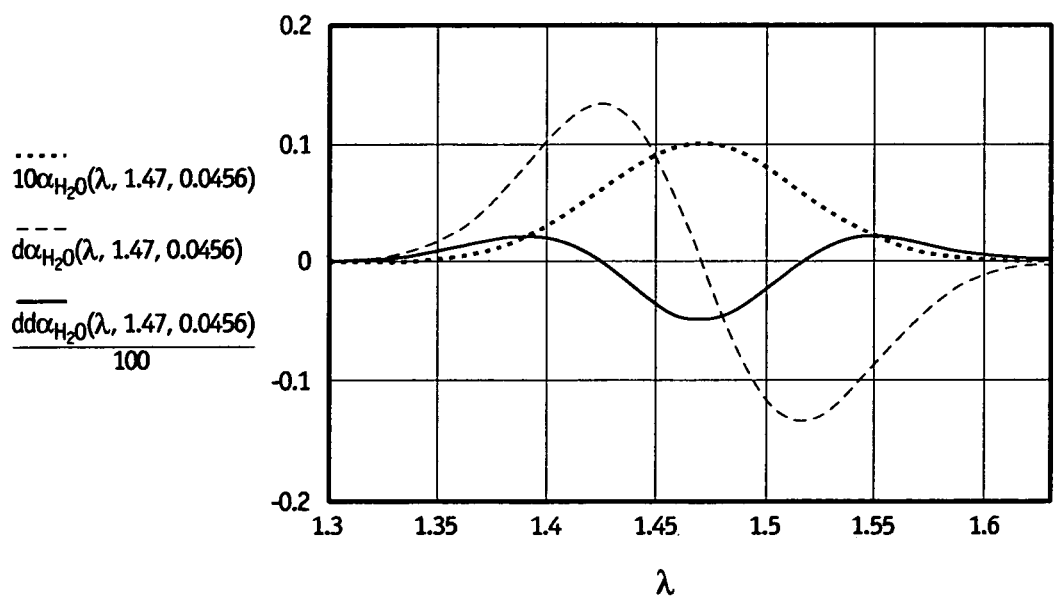
FIG. 2 is a Gaussian line-shape with first and second derivatives.

FIG. 2 shows the Gaussian line-shape along with its first and second derivatives which were calculated by standard numerical analysis. As is apparent, the maximum wavelength of the Gaussian line-shape is also the zero crossing of the first derivative. Given that the absorption peak of water is a function of temperature, that is, the location of the central IR wavelength of the selected moisture peak at 1.9 µm is temperature dependent and has a temperature sensitivity of approximately −0.3 nm per °C., the moisture temperature of a sheet can be inferred by locating the moisture peak. The temperature sensitivity is determined empirically and can be approximated as a linear function within the temperature range that paper experiences within the papermaking process. The wavelength position of the absorption peak is expressed as $\lambda_p = \lambda_0 + (d\lambda/dT) \times \Delta T$, where $\lambda_0$ is the peak position at temperature $T_0$ and $\Delta T$ is the temperature difference from $T_0$, and $d\lambda/dT$ is the temperature sensitivity of the absorption peak (approximately −0.3 nm/°C.).

In operation, the moisture peak at 1.9 µm is initially measured when the moisturized paper sample is maintained at a known temperature. This calibration establishes a baseline temperature ($T_0$) with a corresponding baseline moisture peak wavelength position $\lambda_0$. During actual temperature measurements, the moisture temperature of a product can be inferred by comparing the measured wavelength of the moisture peak to that of the baseline moisture peak and applying the temperature sensitivity of approximately 0.3 nm per °C. By applying the inventive technique, the moisture temperature of a product can be monitored in real time by tracking the location of the maximum wavelength which corresponds to where the first derivative is zero (referred to herein as the "zero derivative") The dependence of the water peak position in paper will not change and is a one time characterization. A further calibration of the scanning wavelength light source is done independently where the drive signal to the scanning wavelength source (for example, a tunable laser diode) is calibrated in terms of emission wavelength using an optical spectrum analyzer.

A preferred non-contact sensor for measuring moisture temperature and which incorporates the inventive technique uses a tunable laser diode as the light source. For sensing moisture in paper, a tunable laser diode enables the sensor to follow the absorption peak as the temperature of the paper being monitored fluctuates. Solid state tunable laser sources in the 1.9 µm wavelength range based on a diode pumped Nd:YAG lasers pumping and optical parametric oscillator (OPO) are commercially available; however, currently these types of sources are less preferred for economic or environmental sensitivity reasons. Tunable laser diodes that generate radiation in the 1.4 to 1.5 µm or 1.9 to 2.0 µm wavelength range are available, for instance, from New Focus (San Jose, Calif.).

When employing the sensor to measure the moisture temperature of a product, one approach is to predetermine the absorption and reference IR wavelengths of interest and to employ the sensor to provide a constant, reliable, stream of energy within the wavelengths. The tunable laser diode allows the emission wavelength to dither around the peak wavelength to obtain the zero derivative and hence temperature. The wavelength position of the zero derivative gives the moisture temperature of the product. The emission wavelength of the tunable laser can be kept on the peak by using a feedback circuit which maintains the derivative held at zero so that the feedback signal is therefore related to the temperature. It should be noted that in practice the magnitude of the moisture peak can change as the moisture content within paper fluctuates. This additional source of variations in the moisture peak can result in errors in the temperature sensor aspect of the inventive combined temperature and moisture sensor. A preferred technique of minimizing these adverse effects is to employed separate temperature independent moisture measurement to correct for the moisture variation component in the tunable laser diode signal so that the tunable laser diode is sensitive only to temperature. A suitable moisture sensor that can be used is described in U.S. patent application Ser. No. 11/116,498 to Haran and Beselt and entitled "Sensor and Methods for Measuring Select Components in Moving Sheet Products," assigned to Honeywell International Inc., which is incorporated herein by reference.

As described above, curve fitting is one technique for analyzing the radiation that emerges from the web to determine the central wavelength position of the radiation of the absorption peak. This process includes (i) measuring a radiation spectrum in a region of the central wavelength position and fitting the spectrum to a function to create a curve, (ii) determining the first derivative of the curve, and (iii) locating the central wavelength from the first derivative on the basis that the first derivative is equal to zero where the central wavelength is at its maximum. In practice, rather than curve fitting, an electronic differentiator or algorithm is used to derive the first derivative. For instance, a web of paper can be scanned with radiation having a defined wavelength of the diode source and the radiation or response signal that emerges from the web is the input waveform to the differentiator. The output waveform from the differentiator is the mathematical derivative of the input waveform. Alternatively, the response signal can be differentiated by passing it through a derivative function constructed in software. The derivative is then fitted to obtain the maximum central wavelength.

In addition, the magnitude of the absorption at the peak wavelength in either reflection or transmission also yields the moisture content of the product. Specifically, since water absorbs radiation across the infrared spectrum as a function of wavelength, the higher the moisture content in a sheet, the less radiation at or near the water absorption peak that will emerge from the sheet.

For measuring water content, the sensor is preferably designed to simultaneously measure the intensity of radiation that emerges, i.e., reflected from or transmitted, from a sheet of paper using the absorption and reference IR band wavelengths. In effect, the absorption measurement at the adsorption IR band wavelength is primarily sensitive to the amount of water in the product and more IR radiation is measured when the product is dry and less infrared radiation when the product is moist. Conversely, for the reference measurement, the radiation is in an IR band wavelength where there is less moisture absorption. The light lost in this band is due to non-water dependent losses from the sheet. These losses are primarily due to scattering from the sheet as well as non-water dependent attenuation factors of the sheet. The reference measurement corrects for non-water dependent losses from the sheet. Note that it is advantageous to have a reference wavelength that is close to the measurement wavelength while remaining outside the water absorption band.

Instead of using a single tunable laser diode, a plurality of fixed or tunable laser diodes or a single multimode laser with distinct but different emission lines can be employed. U.S. patent application Ser. No. 11/116,498 to Haran and Beselt describes a sensor that employs a device that direct infrared radiation from a superluminescent light emitting diode (SLED) or laser diode within specific wavelength bands. This will give a number of discrete points on the absorption line this in conjunction with curve fitting routines can also give the sheet temperature and sheet moisture.

Furthermore, one or more conventional moisture sensors, such as non-contact infrared or microwave devices, can be employed in combination with the inventive moisture temperature sensor. The conventional moisture device would be used in lieu of employing the inventive sensor for measuring moisture in addition to measuring temperature.

Figure 3:
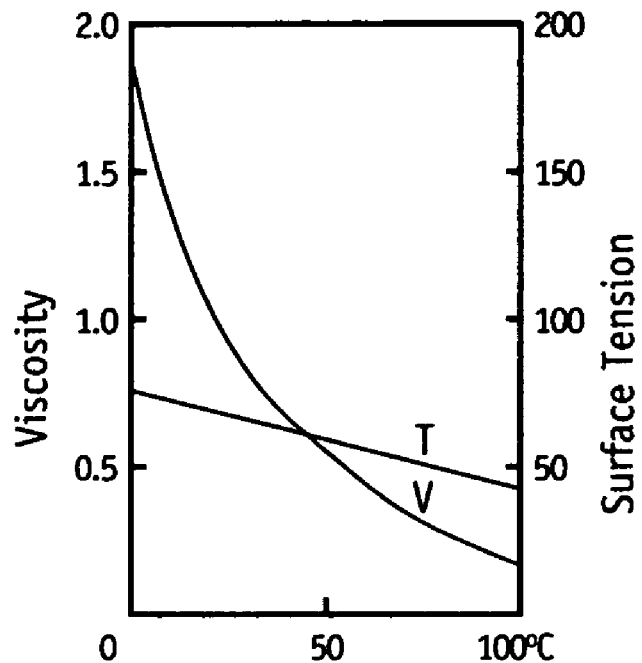
FIG. 3 is a graph showing the temperature dependence of water viscosity and surface tension of water within the paper.

As can be seen from FIG. 3, the temperature of the water in paper affects both the viscosity and surface tension of the water within the paper. In the production of paper, it is often advantageous to increase the sheet temperature in order to reduce its viscosity since it is much easier to press water from the sheet. However, the concomitant reduction in surface tension can weaken the paper which makes the production process more susceptible to sheet breaks. Thus there must be a proper balance of these two characteristics. The moisture temperature and/or with moisture content profiles of the finished products can be obtained with the inventive sensor.

Figure 4:
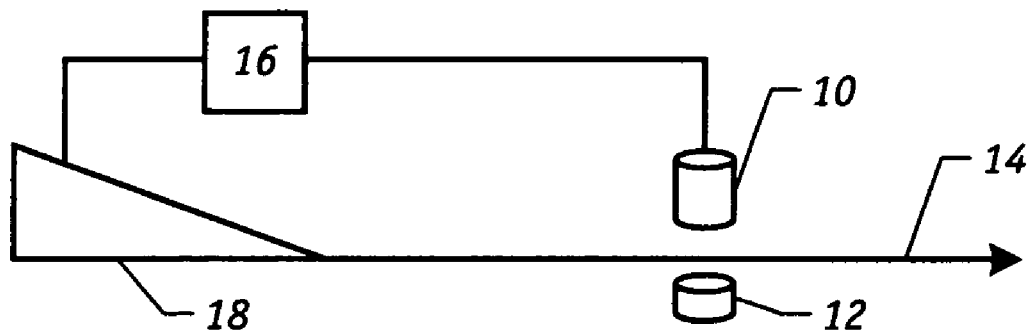
FIG. 4 depicts one configuration of the light source and detection device.

FIG. 4 illustrates an embodiment of the sensor system for measuring the moisture temperature and content of a web 14 which is positionally constrained to travel in a relatively straight line without much fluttering, for instance, by tension or aerodynamics, as in the dry end of a sheetmaking machine. In this case, laser diode as the light source 12 illuminates the lower surface of the web 14 and infrared detector 10. A computer 16 is connected to detector 10 and to actuators of one or more unit operations 18. The computer 16 analyzes the digital images from the detector to estimate the moisture temperature and moisture content of the web 14. In addition, the computer 16 includes a profile analyzer which includes a control system that operates in response to the cross-directional measurements from the detector 10. While this embodiment illustrates the sensor system operating in the transmissive mode, the sensor system can also be configured in the reflective mode where the detector measures radiation that is reflected from the web.

Besides measuring moisture content, other physical characteristics of sheet material can also be monitored. For example, fibers, such as cellulose, latex, minerals, e.g., $CaCO_3$ and clay, and the like can be detected. In each case, selecting the proper radiation regions, e.g., measurement and reference IR bandwidths, is required. IR absorption by different components in paper and paper coated products are further described in U.S. Pat. No. 5,013,403 to Chase, U.S. Pat. No. 5,235,192 to Chase et al., and U.S. Pat. No. 5,795,394 to Belotserkovsky et al., which are incorporated herein by reference.

Figure 5:
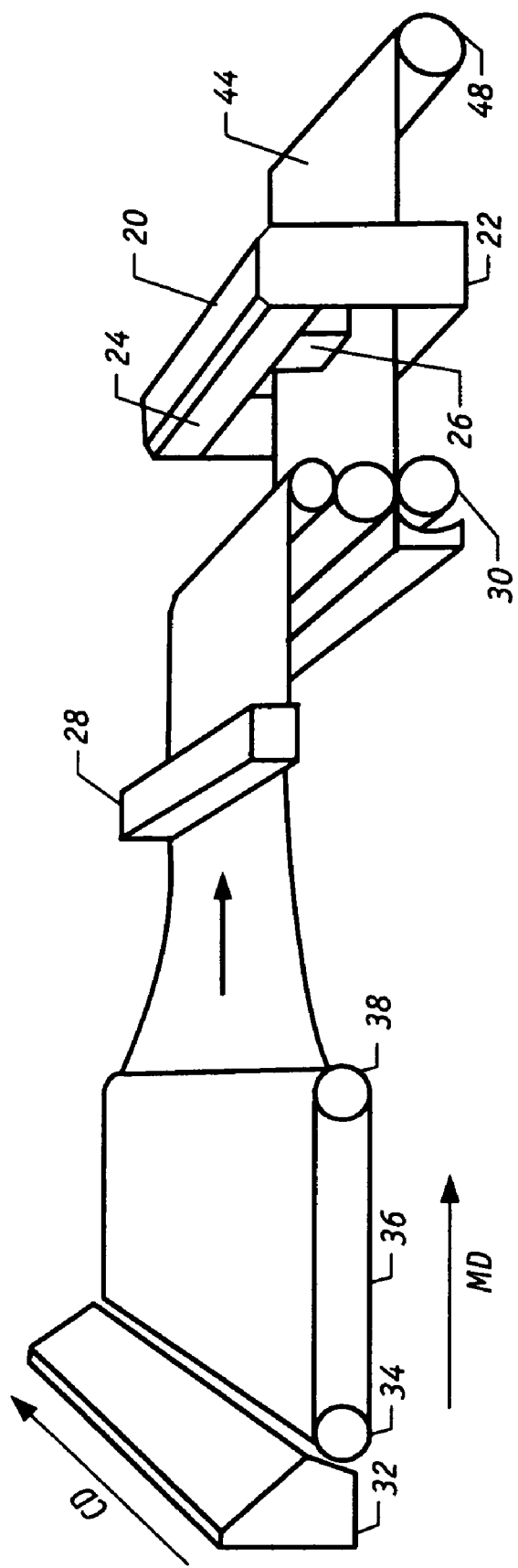
FIG. 5 illustrates a sheetmaking system incorporating the sensor of the present invention.

The inventive sensor is particularly suited for use in a papermaking machine such as that illustrated in FIG. 5. The sheetmaking system for producing a continuous sheet of paper material 44 includes a headbox 32, a steambox 28, a calendaring stack 30, a take-up reel 48 and scanner system 20 that includes the inventive sensor. In the headbox 32, actuators are arranged to control discharge of wetstock onto supporting wire or web 36 along the cross direction. The sheet of fibrous material that forms on top of the wire 36 is trained to travel in the machine direction between rollers 34 and 38 and passes through a calendaring stack 30. The calendaring stack 30 includes actuators that control the compressive pressure applied across the paper web. The sheetmaking system includes a press section (not shown) where water is mechanically removed from the sheet and where the web is consolidated. Thereafter, water is removed by evaporation in the dryer section (not shown). The finished sheet product 44 is collected on a reel 48. In practice, the portion of the papermaking process near a headbox is referred to as the "wet end", while the portion of the process near a take-up reel is referred to as the "dry end".

The scanner system 20 generally includes pairs of horizontally extending guide tracks 24 that span the width of the paper product 44. The guide tracks are supported at their opposite ends by upstanding stanchions 22 and are spaced apart vertically by a distance sufficient to allow clearance for paper product 44 to travel between the tracks. The sensor is secured to a carriage 26 that moves back-and-forth over to paper product 44 as measurements are made. On-line scanning sensor systems for papermaking manufacture are disclosed in U.S. Pat. No. 4,879,471 to Dahlquist, U.S. Pat. No. 5,094,535 to Dahlquist et al., and U.S. Pat. No. 5,166,748 to Dahlquist, all of which are incorporated herein fully by reference.

The inventive sensor system as illustrated in FIG. 4 is particularly suited for moisture temperature and moisture content detection at various locations in the papermaking process in the machine direction and/or cross direction. Sensors can be employed, for instance, along the machine direction over the web to optimize papermaking machines to generate a continuous moisture profile of the paper stock on the web which is compared to an "ideal" profile for making a particular grade of paper. Depending on the degree of deviation from ideal, wet end and/or dry end parameters can be adjusted accordingly. A suitable control process is described in U.S. Pat. No. 6,092,003 to Hagart-Alexander which is incorporated herein by reference. Both dry end parameters, e.g., temperature of heating devices, and wet end parameters can be controlled to achieve the desired final product. Process control techniques for papermaking machines are further described, for instance, in U.S. Pat. No. 6,805,899 to MacHattie et al., U.S. Pat. No. 6,466,839 to Heaven et al., U.S. Pat. No. 6,149,770, to Hu et al., U.S. Pat. No. 6,092,003 to Hagart-Alexander et. al, U.S. Pat. No. 6,080,278 to Heaven et al., U.S. Pat. No. 6,059,931 to Hu et al., U.S. Pat. No. 6,853,543 to Hu et al., and U.S. Pat. No. 5,892,679 to He, which are all incorporated herein by reference.

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A sensor that measures the temperature of a moisture containing composition that comprises:
   (a) an external light source for directing infrared radiation having a desired wavelength region that surrounds an absorption peak for water to be incident upon the composition;
   (b) means for analyzing the infrared radiation that emerges from the composition to determine a central wavelength position or the radiation of the absorption peak; and
   (c) means for computing the moisture temperature from the central wavelength position that includes means for calculating the difference between the determined central wavelength position and a baseline central wavelength position that is determined at a known baseline temperature and means for applying a correlation to determine the temperature of the moisture containing composition.

2. The sensor of claim 1 wherein the means for analyzing the radiation that emerges from the composition includes means for deriving the first derivative of an input waveform representative of the radiation that emerges from the composition.

3. The sensor of claim 1 wherein the external light source is a tunable laser diode.

4. The sensor of claim 3 wherein the tunable laser diode follows the absorption peak as the temperature of the composition fluctuates.

5. The sensor of claim 1 wherein the external light source comprises a plurality of fixed tunable laser diodes.

6. The sensor of claim 1 wherein the external light source comprises a multimode laser diode with distinct but different emission lines.

7. A sensor that measures the temperature and moisture content of a moisture containing composition that comprises:
   (a) an external light source for directing infrared radiation having a desired wavelength region that surrounds an absorption peak for water to be incident upon the composition;
   (b) means for analyzing the radiation that emerges from the composition to determine a central wavelength position of the radiation of the absorption peak;
   (c) means for computing the moisture temperature front the central wavelength position that includes means for calculating the difference between the wavelength position and a baseline central wavelength position determined at a known baseline temperature and means for applying a correlation to determine the moisture temperature; and
   (d) means for measuring the moisture content.

8. The sensor of claim 7 wherein the means for computing the moisture temperature: includes
   (i) means for measuring a radiation spectrum in a region of the central wavelength position and means for fitting the spectrum to a function to create a curve;
   (ii) means for determining the first derivative of the curve; and
   (iii) means for locating the central wavelength from the first derivative on the basis the first derivative is equal to zero where the central wavelength is at its maximum.

9. The sensor of claim 7 wherein die external light source is a tunable laser diode.

10. The sensor of claim 9 wherein the tunable laser diode follows the absorption peak as the temperature of the composition fluctuates.

11. The sensor of claim 7 wherein the external light source comprises a plurality of fixed tunable laser diodes.

12. The sensor of claim 7 wherein the external light source comprises a multimode laser diode with distinct but different emission lines.

13. The sensor of claim 7 wherein the means for measuring the moisture content comprises a non-contact infrared or microwave device.

14. The sensor of claim 13 wherein the wherein the external light source is a tunable laser diode.

15. The sensor of claim 14 wherein the tunable laser diode follows the absorption peak as the temperature of the composition fluctuates.

16. The sensor of claim 13 wherein the external light source comprises a plurality of fixed tunable laser diodes.

17. The sensor of claim 13 wherein the external light source comprises a multimode laser diode with distinct but different emission lines.

* * * * *

UNITED STATES PATENT AND TRADEMARK OFFICE
CERTIFICATE OF CORRECTION

PATENT NO. : 7,494,567 B2
APPLICATION NO. : 11/364930
DATED : February 24, 2009
INVENTOR(S) : Frank M. Haran It is certified that error appears in the above-identified patent and that said Letters Patent is hereby corrected as shown below:

In Column 9, line 18 claim 7, delete "front" and add --from--;
In Column 10, line 6 claim 9, delete "die" and add --the--;
In Column 10, line 19 claim 14, delete "wherein the".

Signed and Sealed this

Fourteenth Day of April, 2009

JOHN DOLL
*Acting Director of the United States Patent and Trademark Office*